United States Patent [19]
Jason

[11] Patent Number: 5,142,358
[45] Date of Patent: Aug. 25, 1992

[54] EARN PER VIEW TELEVISION VIEWING REGULATION DEVICE

[76] Inventor: Leonard A. Jason, 915 W. Schubert Ave. Apt. 1A, Chicago, Ill. 60614

[21] Appl. No.: 653,141

[22] Filed: Feb. 11, 1991

[51] Int. Cl.⁵ .............................................. H04N 7/18
[52] U.S. Cl. ...................................... 358/93; 358/83; 434/247; 364/413.04
[58] Field of Search ............................ 358/93, 190, 83; 434/247; 272/73, 129; 364/413.04; 194/241

[56] References Cited

U.S. PATENT DOCUMENTS

| | | | |
|---|---|---|---|
| 4,298,893 | 11/1981 | Holmes | 358/93 |
| 4,542,897 | 9/1985 | Melton et al. | 272/73 |
| 4,630,817 | 12/1986 | Buckley | 272/73 |
| 4,637,605 | 1/1987 | Ritchie | 272/73 |
| 4,838,404 | 6/1989 | Smith et al. | 194/212 |
| 5,001,632 | 3/1991 | Hall-Tipping | 272/73 |

Primary Examiner—James J. Groody
Assistant Examiner—Michael H. Lee
Attorney, Agent, or Firm—Patula & Associates

[57] ABSTRACT

An earn per view device affording variable viewing on a television as a reward for accomplishment of a positive task on an exercise machine, computer, electronic glove or other associated device. A tabulation and accumulation device tabulates and accumulates the amount of positive task performed on the associated positive task device. A control device for controlling the access to viewing on the associated video device in electrical communication with the tabulation and accumulation device. The control device may be activated the user to afford viewing on the television in proportion to the quantity of positive task accumulated by the tabulation and accumulation device.

18 Claims, 4 Drawing Sheets

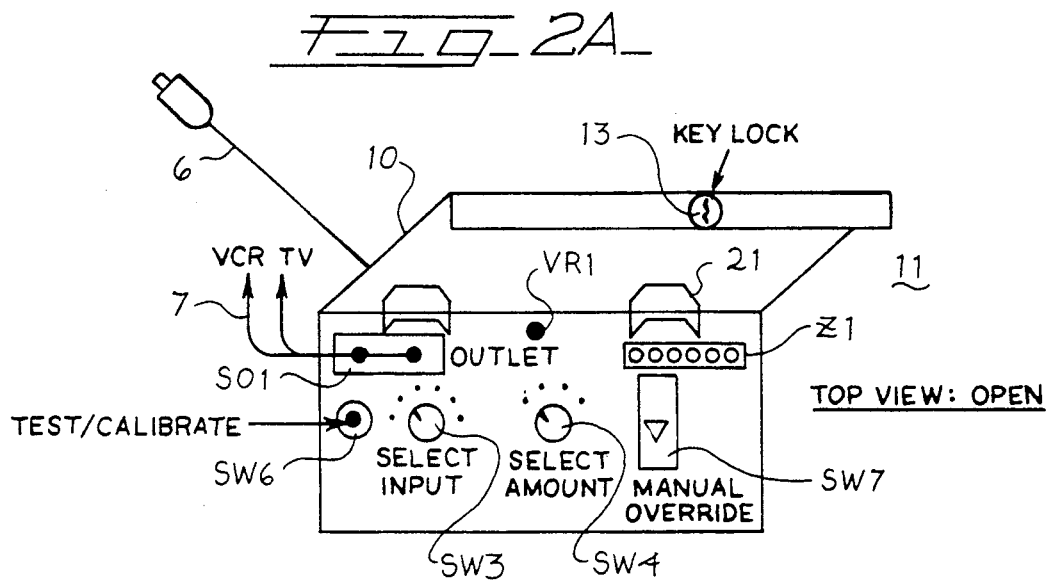
FIG_2A_
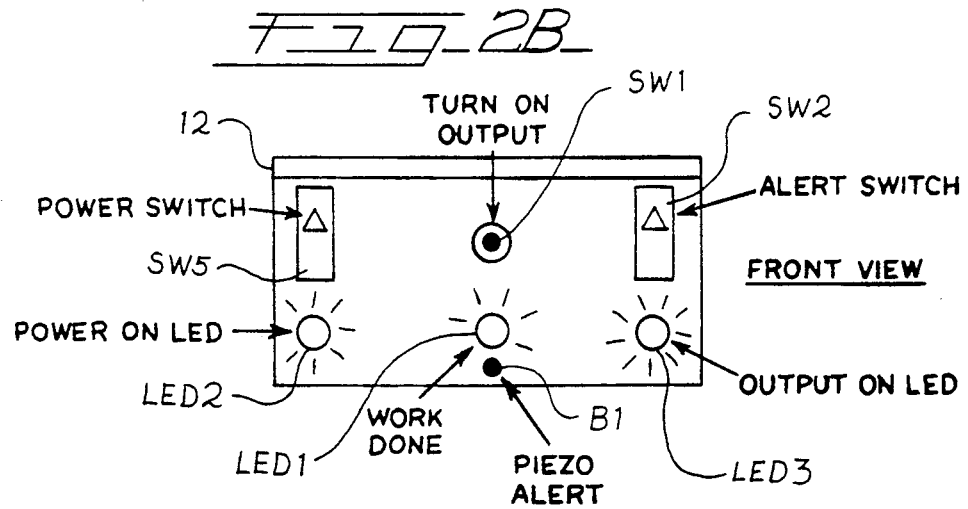
FIG_2B_

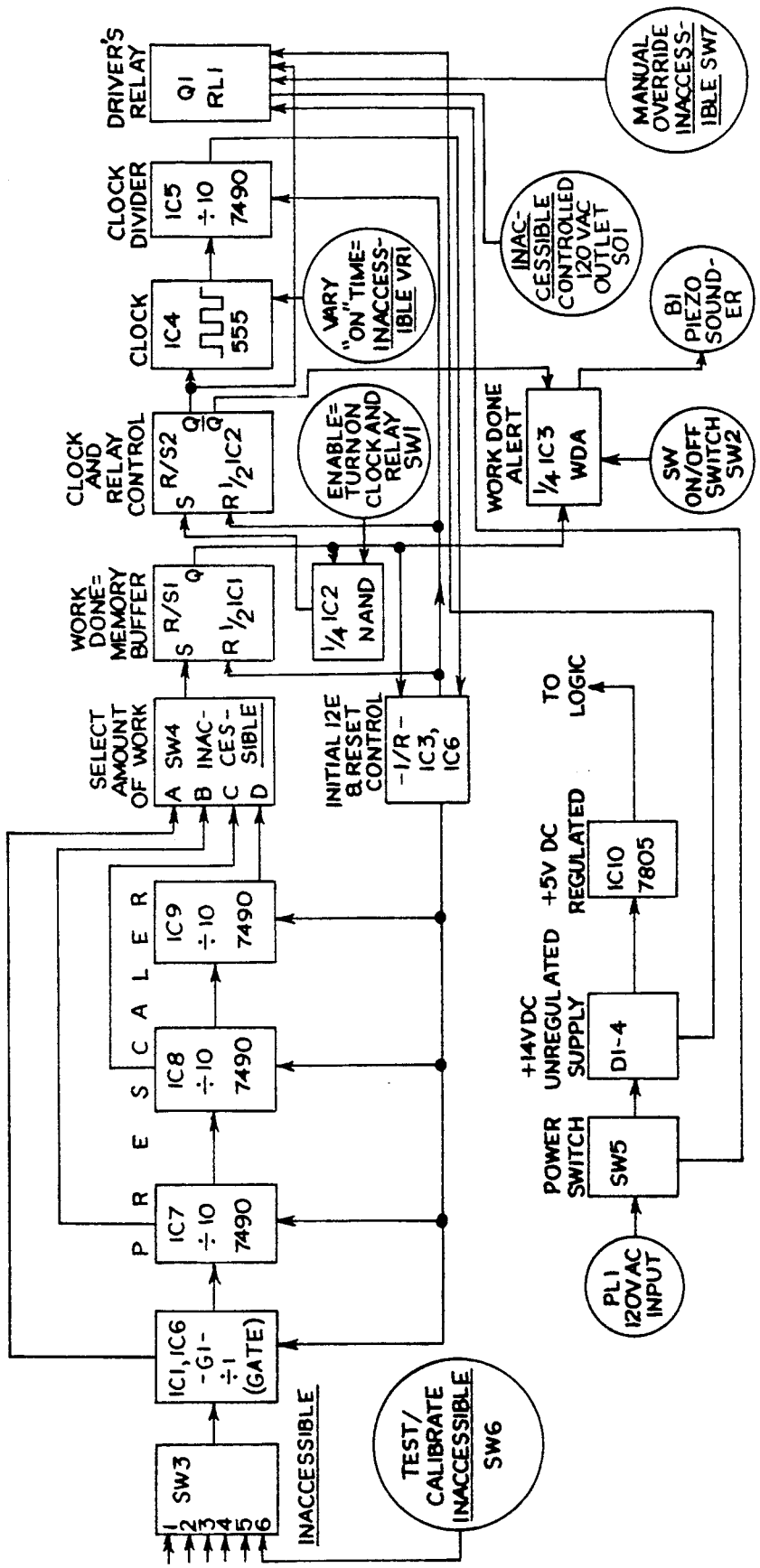

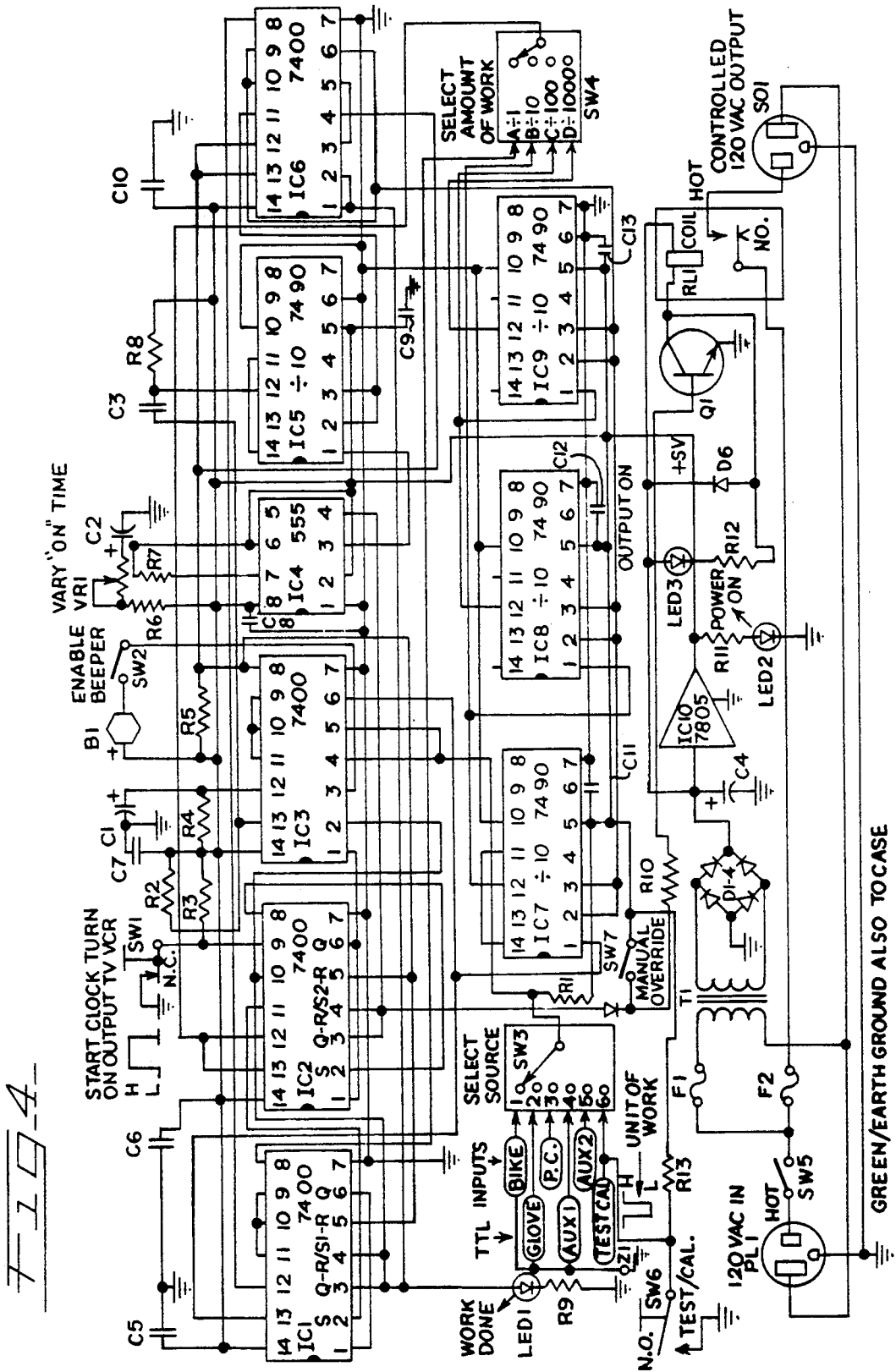

EARN PER VIEW TELEVISION VIEWING REGULATION DEVICE

The invention relates to a device which facilitates the earning, by an individual, of television viewing time in exchange for the performance of a positive task. It is the intended purpose of this invention to reward not just good behavior but for the accomplishment of a specific task.

BACKGROUND OF THE INVENTION

It is a well known fact that children and young adults watch much too much television. In fact, it is a well known fact that when television dominates most of the child leisure time, little time is left for unstructure play activities and for the development of interpersonal skills and friendships.

The extent of violence on television is another valid reason for the concern of many parents about how much television is watched by a child.

There have been devices in the past which attempt to restrict the amount of time television but typically become nothing more than "policeman" type devices which were easily defeated by the child or were typically cumbersome and unproductive to the childs well being. For example, devices such as that disclosed in U.S. Pat. No. 4,566,033 to Reidenouer utilize tokens that require strict parental involvement in not only accessing how much television a particular child is watching but also the physical handing out of tokens be used in metering the time periods to indirectly restrict the television watching activity. Furthermore, in homes with more than one child or in situations with friends and neighbors, the pooling or collective use of tokens defeats the intended purpose of those devices to police or restrict use of television viewing. The present invention proceeds not only to avoid these problems but to perform an entirely different task.

The present invention takes a sophisticated approach of directing and encouraging a child to perform positive tasks and thereby earning television viewing time. This is a vastly different approach than just correcting good behavior as that disclosed in Reidenouer. With devices such as Reidenouer, the parent had to first recognize the good behavior (or the lack of bad behavior) of a child and then enter, either by token or other means, the amount of television viewing time into a device to regulate the amount of television watching available for the child. In an age of both parents working and the commonness of latch-key kids, this obviously is not a workable solution. Especially when there may be many children behaving well and other children who are not performing good tasks that are benefiting by the good behavior of a sibling.

Furthermore, the use of tokens created problems not only having them passed out to the child but problems with the transferring and selling among friends and other family members. Also, the swallowing of the tokens becomes a health concern. The present invention utilizes a totally different concept of various rewardable-earnable tasks which allows variable television viewing ability. It furthermore, and very importantly, provides the advantages to the child that they have their own virtually limitless incentive to earn television watching time based on the performance of various good deeds such as homework and exercise. Also, they would be able to select what to watch and when including the accumulation of such television watching time for use at later times for further enjoyment. All of this is accomplished without the day to day involvement of a guardian/parent to implement the earn-per-view method each day.

The invention claimed herein and described more particularly in the preferred embodiment, relates to an earn-per-view type of television viewing regulation system whereas the interaction between a child and guardian or parent is not necessary to earn or to recognize the earning of television viewing time.

The present invention still affords the flexibility of the parental override not only for lockout, but further to index the television viewing system to afford so much television viewing per the desire of the guardian or parent besides or in addition to the time the child earns to view the television based on their own performance and completion of positive tasks. The present invention also may be manually overriden by the parent to afford unrestricted unaccounted or unearned viewing. This override may be even non-time specific.

It is important to note, that psychologists have found that pursuing a plan in which it rewards not just good behavior but actually the accomplishing of positive specific tasks is highly important to the development of the child and for better family harmony by accomplishing specific tasks around the home.

The tasks that the child may accomplish are many and varied. Some suggested tasks are exercise machines such as rowing machines and stationary bikes, to encourage the child to exercise instead of sitting for long periods of time and watching television. The period of time accomplishing the positive task and thereby earned, provides the appropriate television viewing time.

Furthermore, the use of a computer in which the child does specific homework problems such as learning a foreign language, mathematics, science or grammatical sentence correction, spelling, etc. while using the computer program to be scored as to the accomplishment and completion to provide a certain period of time of television view.

Other types of positive specific tasks may be used to input to the present invention to earn specific time for viewing the television. As shown and described in the preferred embodiment, an exercise bicycle, electronic glove or bilateral motion detector, or personal computer with educational software among other positive tasks can all be inputs to the earning recognition device. The electronic glove may be used with positive tasks such as cleaning, playing educational games or even musical instruments.

It is also understood that the present invention is intended to include many positive tasks which are healthy, helpful and educational as well as enjoyable. The rewards may, as desired, be the ability to play video games, view video tapes or other popular television type activities hopefully are of the type to be productive to the development of a child as well as entertaining.

Numerous other advantages and features of the invention will become readily apparent from the detailed description of the preferred embodiment of the invention, from the claims, and from the accompanying drawings, in which like numerals are employed to designate like parts throughout the same.

BRIEF SUMMARY OF THE INVENTION

An earn per view television regulation device, which recognizes the performance of a positive task such as, but not limited to, exercising or completion of homework on a computer to be tabulated or to accumulate and allow a specific amount of television or prerecorded video tape viewing time porportional to the amount of positive task performed. A quantifiable electronic input is fed into an electronic tabulating and accumulation device which tabulates and accounts for the time accumulated by the child in performing the positive task. Upon reaching either pre-set goals or amount of a task the child desires, the device can allow access, for the appropriate time period, video screen viewing on a television either from broadcast or prerecorded video tape or even video games. The device utilizes conventional hall-effect sensors or other motion devices activated by the child to translate the performed physical motion into a quantifiable electronic signal.

BRIEF DESCRIPTION OF DRAWINGS

A fuller understanding of the foregoing may be had by reference to the accompanying drawings, wherein:

FIG. 2 has perspective views of a preferred embodiment of the prototype in a locking box.

FIG. 3 is a system block diagram of the invention.

FIG. 4 is an electronic schematic/wiring diagram of the invention.

DESCRIPTION AND OPERATION OF PREFERRED EMBODIMENTS

Figure 1:
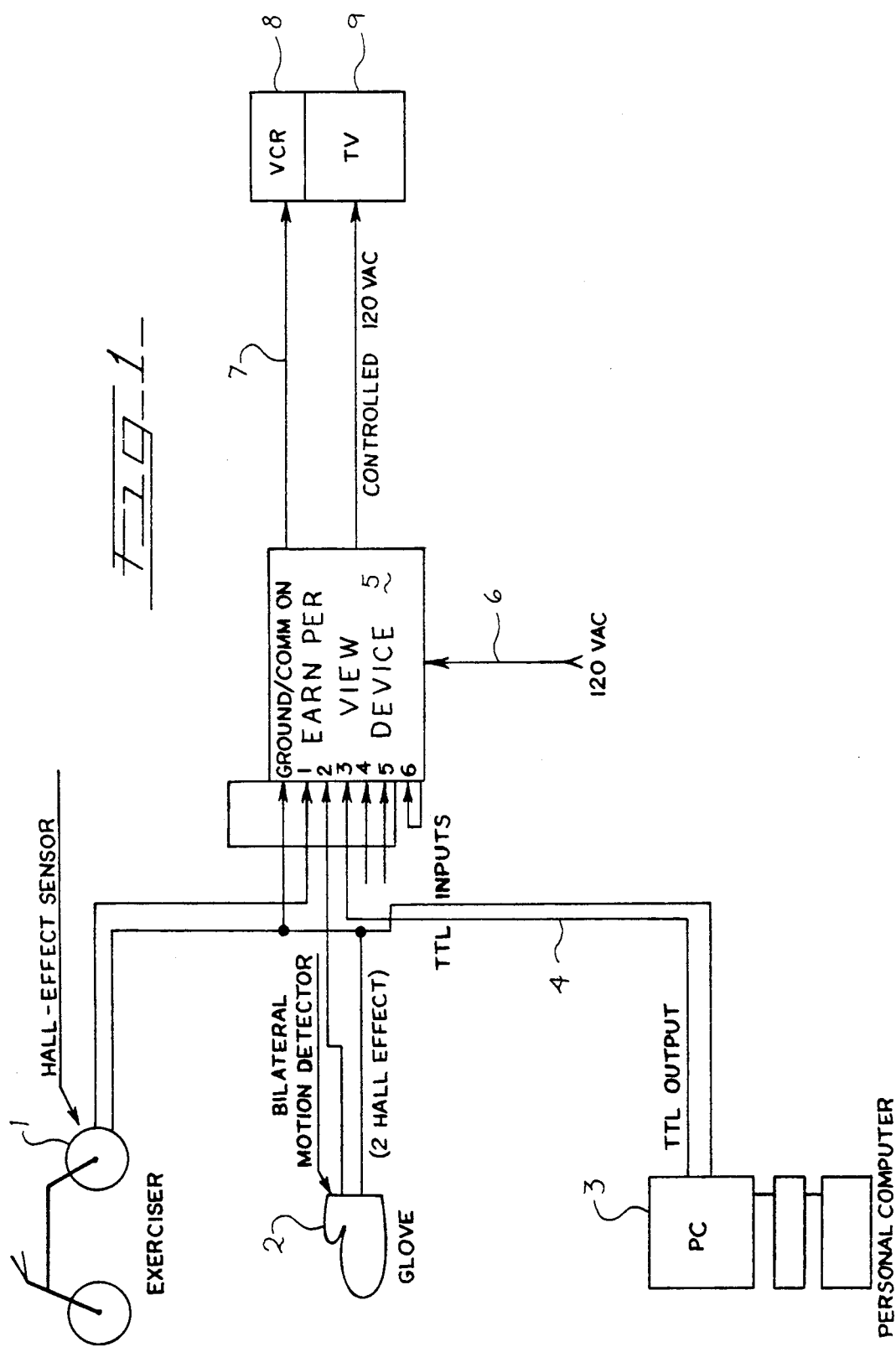
FIG. 1 is a block diagram of input and output equipment connected to the invention as it would be normally used.

While the invention is susceptible of embodiment in many different forms there is shown in the drawings and will be described herein in detail, a preferred embodiment of the invention. It should be understood, however, that the present disclosure is to be considered an exemplification of the principles of the invention and is not intended to limit the spirit and scope of the invention and/or claims of the embodiment illustrated.

FIG. 1 is an overall block diagram of the present invention 5 shows how the system would appear to a user. The present invention 5, the earn per view regulation device has in one the preferred embodiments five external T.T.L. (transistor-transistor logic) input ports 1, 2, 3, 4, 5, and controlled 120 V.A.C. output port connected through cables or wires 7. The positive tasks to be performed by the child, may be an athletic or intellectual task performed on an associated device such as exerciser 1, bilateral motion glove 2, and personal computer 3. In the drawing they are illustrated as external inputs. They are connected to the invention 5 through a twisted pair of wires 4. Internal input port 6 is not accessible to the user; it is a test and calibration position on the input selector. Conventional input power from a 120 VAC outlet is routed through power cord 6 to which the earning of television viewing time. The devices to be controlled in this example are a conventional television 9, and/or a videocassette recorder/player 8.

FIG. 2 shows a preferred embodiment of the invention 5 in two perspective views. In the top view cabinet 11, the output wires 7 are the power cords to the TV 9 and VCR 8 connected to controlled outlet S01. The test/calibrate push button SW6 simulates an external input by giving a minimum of one pulse to the input circuitry. Selector SW3 lets the user determine which input is to be designated. Position 6 is used in conjunction with the test/calibrate button SW6. The amount selected switch SW4 lets the guardian/parent decide (at least initially) how much work is to be performed before the "word done" buffer is set. The selections are done in order of magnitude, from divide by 1 to divide by 1000 in decade steps. Vary "on time" control VR1 lets the guardian/parent select the "on" time duration of the controlled output. This may be directly overridden by the input and timer circuity by toggling the manual override switch SW7 for the duration of their viewing. All of the above controls are in the locked part of the box. The right hinge 21 and left hinge with the identical symbol permit guardian/parental access via key. The key lock 13 lets guardian/parent's program for specific amounts of time or override the entire or partial operation of device 5.

The front view 12 in FIG. 2B, of the device 5 shows controls accessible to children to have certain controls inaccessible to the child and the same will be identified as the same. The master power switch SW5 is shown in the "on" position. Power on LED2 glows when the device 5 is receiving power, turned on, and the low current fuse is in operation. The output enable switch SW1 turns on the controlled outlet S01 for the parentally preprogrammed duration when the work done LED1 is illuminated when the unit has counted the correct number of parentally preprogrammed T.T.L. pulses from an input. If the sounder switch SW2 is on, the Piezoelectric oscillator (sounder) B1 will sound as work done LED1 goes on. The purpose of the sounder is to alert the child that (s)he is ready to be entertained if (s)he cannot directly see the word done LED1. The sounder B1 will automatically be turned off as soon as the output enable SW1 is pressed. B1 does not have to be manually disabled by the sounder switch SW2. The output LED3 and the controlled output S01 will be turned on when the device 5 has: 1) counted the correct number of preprogrammed TTL pulses, and 2) the output has been enabled by pressing the output enable switch SW1.

FIG. 3 Shows an overall system block diagram of the preferred embodiment of the invention. Source select, inaccessible SW3, lets the guardian/parent choose the program or the input source. Test/Calibrate position 6 on SW3 permits the unit to be tested or calibrated. With SW3 in position 6, and when the test and calibrate button (inaccessible) SW6 is pressed, the result is simulated input pulses to the electronic circuitry of the invention.

The input gate G1 lets input pulses into the unit only when it is enabled. G1 will be off during "wake up" initialization. It will also shut off when the unit has detected the correct number of input pulses. This shutoff is so that the work done memory buffer R/S1 can be reset later after the output has been turned off. The shutoff also prevents registering a (false) pulsing input during initialization and giving a false count. G1 goes to position "A" of work select switch (inaccessible) SW4. The output of G1 also goes to a decade divider IC7.

IC7 divides the number of input pulses by 10. 10 units of work (pulses) need to be performed before the child has the option of enabling the output relay. The output of IC7 also goes to the B input of SW4. The output of IC7 also feeds a second decade divider IC8.

The output of IC8 contains the input signal which has been divided by 100. 100 units of work will show a change in the output of IC8. IC8 also goes to input C of SW4. The output of IC8 becomes the input of another decade divider IC9, which also divides by 10. This circuitry is part of the tabulation and accumulation devices provided for in the device 5.

The output of IC9 contains the external input signal divided by 1000, which is fed into input D of SW4.

The output of the work selector SW4 is applied to the set input of the work done memory buffer, reset/set flip-flop R/S1.

R/S1 is a one bit buffer comprised of 2 conventional NAND logic gates. R/S1 becomes set (the Q output goes high) when the set input (denoted By S) is low, and the reset input (denoted by R) stays at the normal high standby state. The Q output of R/S2 is fed into an input of the conventional NAND logic gate, the clock and relay control gate.

NAND logic gate, takes the Q output of R/S1 and the output of SW1, and uses the NAND output to control the clock and relay control R/S2. The NAND logic gate is low when R/S1 is set (high) and simultaneously SW1 is pressed (high).

R/S2 becomes set when the set input (output of the NAND) is low and reset is high. Note that both of these conditions must be met for the controlled output to be enabled. The Q output of R/S2 is fed into the relay driver Q1 and relay RL1.

The output of Q1/RL1 is used to energize the controlled outlet (inaccessible) S01. The path of <SW3, G1, SW4, R/S1, R/S2, Q1/RL1, S01>, is the shortest path which is used to automatically turn on the TV 9 and VCR 8.

R/S2 also feeds the clock IC4. This is an electronic timer which is configured to operate in the stable mode. As long as the input is high, the output will continue to produce pulses which can be varied in duration. The pulse duration is varied by the "vary on time" control (inaccessible) VR1, which acts as a potentiometer that controls the amount of charging current the clock circuit receives. The greater the charging current, the faster a capacitor charges up to a predetermined limit internally set by IC4. Reaching the predetermined limit trips an internal comparator. Tripping the comparator causes the capacitor to discharge through another branch in the circuit. Once that internally predetermined limit has been reached, the cycle starts over. The output of IC4 will then become high again. The output of IC4 if fed into the clock divider IC5.

IC5 divides IC4 clock pulses by 10. 10 pulses are required to make a high to low transition in the output of IC5. Once 10 pulses have been counted, the initialization reset control I/R will reset the whole device 5. The reset pulse comes from the output of IC5.

Once I/R has the signal to reset, the output of I/R goes how and stays low to G1, IC7, IC8, and IC9, permitting them to count inputs again. The input gate and prescaler (scaling the application to the device 5) is turned off while the output S01 is on. The turnoff is so the set input of R/S1 remains high, thus allowing R/S1 to be reset when the predetermined cycle at IC10 has elapsed. The other output of I/R resets R/S2 by causing the reset input to go low very momentarily. It also resets IC5 to bi-quinary 0000 internally. The device 5 is now ready to start another cycle counting input pulses. The I/R also performs the same functions automatically when the device 5 "wakes up". This initialization sequence, which is on the order of less than 100 milliseconds, forces all registers to be reset. This reset is required so that R/S1 or R/S2 do not "wake up" in ambiguous states. Initialization also forces the whole system into reset for the duration that power supply and switching transients can take to settle down. These transients could cause false signaling inside the device, which would cause erratic or improper operation.

The manual override switch (inaccessible) SW6, lets the guardian/parent(s) open the top of the device 5 and toggle SW6. Toggling SW6 will manually turn on the output relay and socket S01. S01 will stay on until SW6 is toggled to the previous "off" position.

The work done alert circuitry ("WDA") enables the piezo sounder B1 if R/S1 is set and R/S2 is reset. The sounder lets the child know that (s)he can turn on the TV 9/VCR 8, and also that no further amount of work will be stored in the device 5. WDA circuitry will be especially useful for children working outside by an open window. B1 can be manually disabled by toggling the on/off switch SW2 to its other position.

Operative power is provided through power cord 6 and plug PL1. PL1 goes to the master power switch SW5. SW5 goes to the output relay RL1.

The control circuitry to afford power to the associated television or device is configured in part as follows. The hot switched 120 VAC is also applied to the 14 volt supply D1-4, which has a transformer, and bridge rectifier comprised of diodes D1-4. This also includes a filter capacitor. The out put of D1-4 at 14 VDC is used to power the relay coil to provide positive switching action. D1-4 is also applied to a positive voltage regulator IC10. IC10 provides a standard 5 volts D.C. regulated for all of the logic electronic circuitry.

Depicted in FIG. 4 is a complete schematic diagram of the device 5 and specifically the recognition, control and tabulation or accumulative circuitry of the present invention. IC1, IC2, IC3, and IC6 are all generic conventional digital T.T.L. type 7400 quad NAND gates. IC4 is a generic conventional type 555 timer. IC5, IC7, IC8 and IC9 are all generic conventional digital TTL type 7490 decade counters. IC10 is a generic conventional type of 7805 linear positive voltage regulator. Q1 is a generic type 2N2222 NPN transistor. All diodes D1-6 are generic conventional 1 ampere rectifier diodes. LED1, LED2 and LED3 are generic red LED's. B1 is a generic type piezo-oscillator unit operating on 5 VDC. T1 is a generic transformer having 12 VAC output at 300 milliamperes. RL1 is a generic type relay with a 12 volt/low current coil and 12 VAC controlled output with a current rating higher than fuse F2. Bypass capacitors C5-13 are used as a safety means to prevent signal glitches by smoothing out any transients.

Only ½ of IC1 is used to configure or make R/S1. This R/S flip-flop is made by connecting the outputs of the 2 NAND gates used to each other's gate input. The unused NAND inputs become the inputs to the flip-flop. The output of the set input (pin 2) is Q (pin 3); The reset (Pin 5) output is not Q (pin 6). LED1 goes on when R/S1 has been set. R9 limits the current through LED1. The other half of IC1 is used to make up an "AND" gate which is part of G1 (see FIG. 3). Pins 13 and 12 are inputs to a NAND gate. The output (pin 11) is fed into pin 10, an input to another NAND gate, pins 9 and 10 are tied together, forming an invertor. This together forms the "AND" gate.

IC2 also has an R/S Flip-Flop, R/S2, with exactly the same configuration as R/S1. Pins 13, 12 and 11 are configured to form an invertor, the output of which is used to invert the output of the work amount switch. Pins 10, 9 and 8 are part of the gated enable circuitry for R/S2. The Q output of R/S1 is fed into pin 10. The output of SW1 is held low. When SW1 is pressed, pin 9 is forced high. This high makes pin 8 low, which sets R/S2, starting IC4 to cycle, which lets the child use up the earned time to view at his/her convenience, not necessarily right after earning the work that has been performed. R3 is a pullup resistor for the pin 9 input.

IC3 performs part of the initialize and system reset control operation; also logic switching of the work done alert control. It also inverts the input pulses so that if the external input equipment 1, 2 or 3 is turned off (high impedance input), the unit will not automatically register an input. The input is at pins 4 and 5; the inverted output is pin 6. C1 is a short circuit at "wakeup". It effectively grounds pin 12 forcing it low. The output of this NAND gate (pin 11) will always be high during wakeup. Pin1 1 is fed into pin 10. Pin 10 is also connected to pin 9, making this other NAND gate an invertor. Together both NAND gates form an "AND" gate. With the input of the "AND" gate being forced low during wake-up, the output of the "and" gate will always be low until C1 charges up to greater than 0.8 VDC. The output (pin 8) is connected to the reset inputs of R/S21 and R/S2. It is also connected to pins 4, 13, and 12 of IC6. R5 is a pullup resistor for the system reset line, which adds noise immunity to prevent false signal glitches. Pin 1 has R/S2's not Q output, while Pin 2 has R/S1'1 Q output. When R/S1 has been set, and R/S2 is reset, both inputs will be high. This will force the output pin 3 low, presenting a ground to the right side of SW2. If SW2 is on, B1 will be grounded, and will sound. The alert will sound when work has been done, but will be automatically turned off as soon as the output S01 is turned on by pressing SW1.

IC4 is the clock. This generates a series of square waves lasting in duration from about 0.7 minutes to 15 minutes. The first cycle will last longer since C2's voltage is near ground potential at the start of a new system cycle. R6 limits the minimum charging current or minimum cycle time. VR1 lets the guardian/parent choose how long the system output will be on. R7 limits discharge current and assures that the oscillator will start. The conductor from pin 6 to pin 2 lets the internal flip-flop be triggered on. This triggering will make the output high while allowing the capacitor to charge. After C2 attains a level at ⅔ of supply voltage, pin 3 goes low; an internal transistor is switched on to discharge C2. When C2 is discharged, the output again goes high, while C2 starts charging. Pin 4 is a reset for IC4. When Q (Pin 3) of R/S1 is high, pin 4 on ICr will be high. Then IC4 will be in the active stable mode, producing square waves of preprogrammed duration. Pin 3 is the output, feeding input pin 1 of IC5.

IC5 divides the pulses of the 555 time chip or clock to effectively increase the range of the timer by 10. This makes it possible to use a generic filter capacitor for C2. The leakage of C2 is much less than the minimum charging current through VR1, which is also made generic. Pins 2 and 3 (P)reset the counter to bi-quinary 0000 when they are high. They are made high from control logic in IC6 during wake-up and immediately when R/S1 is set. Preset 9 (pin 6) is grounded for normal operation. Pin 11 is connected to Pin 14 to configure the divider to count in a bi-quinary sequence. The QA [MSB] output (pin 12) will show a high to low transition when the counter goes from one decade to the next. This low output is coupled through C3 to pin 13 of IC3, which will see an immediate low, resetting R/S1 and R/S2. These resets will remain low until C3 charges up through pullup resistors R2 and R8, allowing Pin 13 of IC3 become high.

IC6 performs gate, initialization, and reset functions. The reset line is fed into pins 13 and 12, forming an inverted reset (pin 11). Pin 11 is fed into pins 2 and 3 of IC5, causing IC5 to be reset to bi-quinary 000 when the system reset line is active low. Pin 4 contains the system reset signal, while pin 5 has the R/S1 not a Q signal. The output (Pin 6) is fed to pins 2 and 3 of IC7, IC8, and IC9. This will be high causing IC7, IC8 and IC9 to reset to bi-quinary 0000. This condition will be met when R/S1 has become set, and will later need to be reset; "or" goes high during initialization when the system reset line is being forced low. This one-legged inverted NAND is logically equivalent to an "OR" gate with the other input leg inverted. This output is fed to pins 10 and 9 of IC6, forcing the output pin 8 low when the prescaler counters' reset is high. This output is fed to pin 12 of IC1, turning off the transmission gate G1 when the prescaler is in the reset mode 000.

All external inputs must be TTL compatible. All positive task inputs from the associated devices 1, 2 and 3 are fed to a rotary switch source select SW3 through a conventional barrier terminal strip Z1. In this embodiment of the invention 5, a high to low to high TTL pulse at Z1 will be defined as one unit of work.

The output of SW3 goes to IC1 for the divide by 1 transmission gate and IC7's clock pulse (CP) input. IC7, IC8, and IC9 are all configured to divide their respective Cp inputs by 10 to cause a high to low transition at pin 12 by the connection from pin 11 to pin 14. Pin 12, which divides the input by 10, is fed into the amount of work selector SW4 at position B. It is also fed to input pin 1 of IC8. Similarly the output of IC8 which is now divided by 100 is fed to position C of SW4 and the input pin 1 of IC9, the output pin 12 of IC9 contains the input signal at SW3 divided by 1000. This output feeds position D of SW4. BY selecting position D, 1000 units of work need to be performed to set R/S1. A test/calibration option is built into the device 5. By setting SW3 to position 6 and pressing SW6, at least one unit of work is simulated which will set R/S1 and light LED1. Then SW1 can be pressed which will turn on the power relay, LED 3, and controlled outlet S01.

The devices is operationally powered through power cord PL1. This is a three-terminal plug with the conventional standard earth ground conductor, rated greater than the combined capacity of fuses F1+F2. The hot conductor of PL1 is routed to main power switch SW5. Fuse F2 protects all controlled output stages. The low current fuse F1 protects the power supply and logic. Power transformer T1 takes the 12 VAC and reduces it to a safe 12 VAC. The output of T1 feeds a full-wave bridge rectifier D1–D4. Filter capacitor C4 is tied to the rectifier output to prefilter the raw D.C. for the voltage regulator IC10 so that IC10 will regulate properly. C4 also prevents modulation of the output relay RL1 and controlled output S01. LED2 is on when the power supply is energized. Resistor R11 limited LED1's current to a safe value. The regulator output drives all of the logic circuitry.

The Q output (pin 3) of IC2 is used to switch on the output S01. The Q output signal goes through diode D5. D5 prevents current through the manual override switch SW7 from damaging the Q output stage of IC2 when Q is active low. Transistor Q1 forms the relay driver. R10 limits base Drive 10 Q1. When the base of Q1 is high, the collector becomes low. This low collector lets unregulated current flow from the anode of C4 into the relay coil RL1 and to the low collector of Q1. This current causes RL1 and the output indicator LED3 to energize. Resistor R12 limits LED3's current. Diode D6 prevents RL1's reverse voltage spike from damaging Q1 or LED3.

The operation of the preferred embodiment is simply and effectively described as follows. Referring to FIGS. 1 and 2, the guardian/parent will plug in the power cord 6 into a conventional 110 VAC power source. The inventive device 5 is turned on at power switch SW5. Power on Indicator LED2 will illuminate. The guardian/parent can test the manual override circuitry and switch SW7 by toggling it back and forth. Output on indicator LED3 should follow the toggling. The guardian/parent then turns the manual override of SW7 off.

Then the guardian/parent can then select the test position 6 on select input switch SW3. The test/cal enable switch SW6 may be pressed in which the work done light emitting indicator LED1 will illuminate. If the work done sound emitting device B1 is switched on at switch SW2, the alert will also sound.

To test or calibrate the timer circuitry; the output enable switch SW1. The output on indicator LED2 should light. Now the clock is counting down. It can be timed to be calibrated at variable control VR1. Now that the device 5 has been tested and calibrated, power switch SW5 is turned off.

The user connects positive athletic or intellectual task devices to the external TTL or work earned inputs (hot side) to positions 1-5 on the barrier terminal strip Z1. All inputs must be high for no lack of an input. The user then connects all equipment grounds to the common ground terminal on the terminal strip Z1. The positive tasks equipment 1, 2, 3 should be powered up or activated first (in case external signal communication glitches appear).

The guardian/parent selects the settings for SW3, SW4, SW7, and SW2 as discussed above. After setting the appropriate switches, the top may be locked 13. This setting is optional as per the guardian/parent.

The power switch SW5 is turned on in which power on LED2 will illuminate. The child then performs the positive task on the exerciser 1, glove 2 or computer 3 as in the preferred embodiment or some other external input can be selected. The circuitry described above is recognized and tabulated. The accumulation circuitry accounts for and stores the amount of task performance. LED1 lights (B1 sounds if SW2 is on), the child may then press SW1 at any time to turn on the output TV 9 or VCR 8. This function is part of the control circuitry described above. The child is under no time constraints to watch TV 9 or the VCR 8 at any time. "Output On" LED 2 will then illuminate.

After the preprogrammed time period has elapsed, the output, LED1, and LED3 will go off. The child may now earn more television viewing time by earning through the performing of additional activities on exerciser 1, glove 2 or personal computer 3 which would retrigger work done LED1.

It is understood that these cycles may be continued infinitely. If the guardian/parent wants to watch the television 9 or VCR 8 without this system in place, (s)/he merely unlocks the top of the unit and toggles the manual override switch SW7. Toggling SW7 will turn the TV 9/VCR 8 on for as long as the switch is in this position. SW7 overrides all other timer functions in the device 5.

It is understood that within the scope and spirit of the claimed invention, that multiple devices 5 such as that described in the preferred embodiment, can be placed in parallel with specific rewardable tasks and reward devices such as television(s), video cassette recorder player(s), or video game(s), either in the same cabinet or separately for use with multi-child applications. Furthermore, greater or lesser parental/guardian control such as when or how much viewing will be allowed, can be readily configured in the device 5 of the present invention.

The foregoing specification describes only one of the preferred embodiment of the invention as shown. Other embodiments besides the one described, shown and claimed may be articulated as well. The terms and expressions therefore serve only to describe the invention by example only and not to limit the invention. It is expected that others will perceive differences which while differing from the foregoing, do not depart from the spirit and scope of the invention herein described and claimed.

What is claimed:

1. An earn per view device affording variable viewing on an associated video device as a reward for the accomplishment of a positive task on an associated device said performed without the use of a coin, currency, or its equivalent, comprising:
   tabulation and accumulation means for tabulating and accumulating the quantity of the positive task on the associated device; and
   control means for controlling the amount of viewing on the associated video device, in electrical communication with said tabulation and accumulation means, whereby said control means activated by the user to afford viewing on the associated video device in proportion to quantity of positive task accumulated by said tabulation and accumulation means.

2. The device of claim 1, wherein said tabulating and accumulation means is variable in proportion of positive task performed on the associated device to viewing on the associated video device.

3. The device of claim 1, wherein said control means is overridable to afford viewing on the associated video device without regard to said tabulation and accumulation means.

4. The device of claim 1, wherein said tabulating and accumulation means is variably pre-set to specific levels of positive task performance performed on the associated device to afford pre-set amounts of viewing on the associated video device.

5. The device of claim 4, wherein said earn per view device further comprises sound emitting means when specific level of positive task performance is achieved by tabulation and accumulation by said tabulation and accumulation means.

6. The earn per view device of claim 4, wherein said device further comprises light-emitting means when specific level of positive task performance is achieved by tabulation and accumulation by said tabulation and accumulation means.

7. An earn per view television viewing device affording variable access to television or other video source as a reward for the accomplishment of an athletic or intellectual task on an associated athletic or intellectual device said performed without the use of a coin, currency, or its equivalent, comprising:

recognition and control means for recognizing the accomplishment of an athletic or intellectual task from the associated or intellectual device; and tabulation means for accounting for the accomplishment of an athletic or intellectual task, in electrical communication with said recognition and control means, whereby said recognition and control means activated by the user to provide access to the television or other video source in proportion to the amount of athletic or intellectual task accomplished as accounted for by said tabulation means.

8. The device of claim 7, wherein said tabulation means is variable in proportion of athletic or intellectual task performed on the associated device to access to television or other video source.

9. The device of claim 7, wherein said recognition and control means is overridable to afford access to television or other video source without regard to said tabulation and accumulation means.

10. The device of claim 7, wherein said tabulation means is variably pre-set to specific levels of athletic or intellectual task performance on the associated device to afford pre-set amounts of access to television or other video source.

11. The device of claim 10, wherein said earn per view device further comprises sound emitting means when specific level of athletic or intellectual task performance is achieved by tabulation by said tabulation means.

12. The device of claim 10, wherein said earn per view device further comprises light emitting means when specific level of athletic or intellectual task performance is achieved by tabulation by said tabulation means.

13. A method of affording variable viewing on an associated video device as a reward for the accomplishment of a positive task on an associated device said performed without the use of a coin, currency, or its equivalent, comprising the steps of:

performing a positive task on an associated device which is tabulated by tabulation means;

accumulating the amount of the positive task tabulated by said tabulation means in accumulation means, said accumulation means in communication with said tabulation means;

affording viewing on an associated video device in proportion to the amount of the positive task accumulated in said accumulation means by control means for affording viewing on an associated video device, said control means in communication with said accumulation means.

14. The method of claim 13, wherein said tabulation means is variable in proportion of positive task performed on the associated device to viewing on the associated video device.

15. The method of claim 13, wherein said control means is overridable to afford viewing on the associated video device without regard to said accumulation means.

16. The method of claim 13, wherein said accumulation means is variably pre-set to specific levels of positive task performance on the associated device to afford pre-set amounts of viewing on the associated video device.

17. The method of claim 16, further comprising the step of emitting sound from sound emitting means when specific level of positive task performance is accumulated by said accumulation means.

18. The method of claim 16, further comprising the step of emitting light from light emitting means when specific level of positive task performance is accumulated by said accumulation means.

* * * * *